United States Patent
Ferro et al.

(10) Patent No.: US 11,957,189 B2
(45) Date of Patent: Apr. 16, 2024

(54) SYSTEM AND METHOD FOR ENHANCING STERILITY

(71) Applicant: AOD Holdings, LLC, Arroyo Grande, CA (US)

(72) Inventors: Thomas Ferro, Arroyo Grande, CA (US); Austin T. Ferro, Arroyo Grande, CA (US); Joseph R. Phillips, Paso Robles, CA (US)

(73) Assignee: AOD Holdings, LLC, Arroyo Grande, CA (US)

( * ) Notice: Subject to any disclaimer, the term of this patent is extended or adjusted under 35 U.S.C. 154(b) by 192 days.

(21) Appl. No.: 15/455,982

(22) Filed: Mar. 10, 2017

(65) Prior Publication Data

US 2018/0255846 A1    Sep. 13, 2018

(51) Int. Cl.

| | |
|---|---|
| *A41D 13/00* | (2006.01) |
| *A41D 13/12* | (2006.01) |
| *A41D 19/00* | (2006.01) |
| *A61B 42/10* | (2016.01) |
| *A61B 42/40* | (2016.01) |

(52) U.S. Cl.
CPC ..... *A41D 13/0005* (2013.01); *A41D 13/1209* (2013.01); *A41D 19/0055* (2013.01); *A61B 42/10* (2016.02); *A61B 42/40* (2016.02)

(58) Field of Classification Search
CPC ............ A41D 13/0005; A41D 13/1209; A61B 42/10; A61B 42/40
See application file for complete search history.

(56) References Cited

U.S. PATENT DOCUMENTS

| | | | | |
|---|---|---|---|---|
| 2,030,135 | A * | 2/1936 | Carpenter | G09F 15/02 2/338 |
| 2,248,303 | A * | 7/1941 | Morgenroth | A61F 13/064 128/893 |
| 2,292,024 | A * | 8/1942 | Dreher | G09F 3/10 301/5.21 |
| 2,730,720 | A * | 1/1956 | Saunders | A42B 1/12 2/68 |
| 3,009,164 | A * | 11/1961 | Frey | A41D 19/0089 2/270 |
| 3,480,012 | A * | 11/1969 | Smithers | A61F 13/06 128/DIG. 15 |
| 3,503,078 | A * | 3/1970 | Gallian | A41B 11/12 2/311 |
| 3,555,564 | A * | 1/1971 | Miskell et al. | A41D 19/0062 2/168 |
| 3,793,110 | A * | 2/1974 | Saunders | B29C 66/004 156/289 |

(Continued)

*Primary Examiner* — Richale L Quinn
(74) *Attorney, Agent, or Firm* — McDonnell Boehnen Hulbert & Berghoff LLP

(57) ABSTRACT

A system for enhancing sterility. The system includes a first surgical glove comprising an upper glove portion and a lower glove portion. A surgical garment comprising at least one surgical garment cuff, and a sealing device comprising a first adhesive. The first adhesive of the sealing device is configured to be affixed between an inside surface of the lower portion of the first surgical glove and an outside surface of the at least one surgical garment cuff so as to provide a fluid seal between the first surgical glove and the at least one surgical garment cuff of the surgical garment.

10 Claims, 4 Drawing Sheets

(56) References Cited

U.S. PATENT DOCUMENTS

| | | | | |
|---|---|---|---|---|
| 4,078,266 A * | 3/1978 | Brown | A41B 11/00 | 602/30 |
| 4,884,300 A * | 12/1989 | Vistins | A41D 19/0082 | 2/160 |
| 4,947,868 A * | 8/1990 | Schoolman | A41D 13/1209 | 604/304 |
| 5,020,159 A * | 6/1991 | Hellickson | A41D 19/0075 | 2/167 |
| 5,033,115 A * | 7/1991 | Bowling | A41D 13/11 | 2/48 |
| 5,073,988 A * | 12/1991 | Lewis, Jr. | A41D 19/0041 | 2/270 |
| 5,152,282 A * | 10/1992 | Elphick | A61F 13/041 | 602/57 |
| 5,467,483 A * | 11/1995 | Saadatmanesh | A41D 19/0082 | 2/161.7 |
| 5,515,544 A * | 5/1996 | Hosking | A41F 5/00 | 2/112 |
| 5,572,743 A * | 11/1996 | Yavitz | A41D 13/1209 | 2/125 |
| 5,594,955 A * | 1/1997 | Sommers | A41D 13/1227 | 2/114 |
| 5,628,067 A | 5/1997 | Meyer et al. | | |
| 5,680,653 A * | 10/1997 | Mathis | A41D 31/102 | 2/114 |
| 5,693,401 A * | 12/1997 | Sommers | A41D 19/0089 | 24/442 |
| 5,749,098 A * | 5/1998 | Evans | A41D 19/0041 | 2/124 |
| 5,802,612 A * | 9/1998 | Hosking | A41F 5/00 | 2/112 |
| 5,867,832 A * | 2/1999 | Liu | A41D 19/0055 | 2/161.7 |
| 5,909,801 A * | 6/1999 | Coffman | A41D 19/0041 | 2/16 |
| 5,924,130 A * | 7/1999 | Fragomeli | A41D 13/0005 | 2/16 |
| 6,155,263 A * | 12/2000 | Weaver | A41D 13/08 | 128/878 |
| 6,301,755 B1 * | 10/2001 | Gaber | A41D 13/129 | 24/442 |
| 6,665,880 B2 * | 12/2003 | Poppe | A41D 27/10 | 2/114 |
| 7,051,374 B1 * | 5/2006 | Grilliot | A41F 1/002 | 2/69 |
| 7,246,382 B2 * | 7/2007 | Plut | A41D 19/0055 | 223/111 |
| 7,383,588 B2 * | 6/2008 | Victor | A41D 20/00 | 2/22 |
| 7,467,424 B2 * | 12/2008 | Sokoloff | A41F 17/02 | 2/232 |
| 7,624,455 B1 * | 12/2009 | Bhalla | A41D 19/0055 | 2/160 |
| 7,665,150 B2 * | 2/2010 | Holley | A41D 19/0044 | 2/161.7 |
| 7,685,649 B2 * | 3/2010 | Jordan | A41D 13/1209 | 2/457 |
| 8,015,622 B1 * | 9/2011 | Bhalla | A41D 19/0044 | 2/160 |
| 8,151,373 B2 * | 4/2012 | Pando | A41F 1/06 | 2/161.6 |
| 8,167,337 B2 * | 5/2012 | Bruno | F16L 37/04 | 285/7 |
| 8,341,768 B2 * | 1/2013 | Gellerstedt | A41D 13/1209 | 2/160 |
| 9,113,666 B2 * | 8/2015 | George | A41D 19/0044 | |
| 9,464,213 B2 * | 10/2016 | Taha | C09J 7/21 | |
| 9,498,010 B2 * | 11/2016 | Tuttle | A61F 15/004 | |
| 9,538,792 B2 * | 1/2017 | Essery | A41B 9/02 | |
| 10,004,282 B2 * | 6/2018 | Taha | A61B 42/10 | |
| 10,165,814 B2 * | 1/2019 | Thompson | A41D 19/0041 | |
| 11,388,937 B2 * | 7/2022 | Nachawati | A41D 31/02 | |
| 2002/0189007 A1 * | 12/2002 | Cormier | A41D 19/0089 | 2/457 |
| 2003/0046748 A1 * | 3/2003 | Tanenbaum | A41D 19/0089 | 2/209.13 |
| 2004/0099666 A1 * | 5/2004 | Ordiway | B65D 41/22 | 220/359.1 |
| 2004/0123367 A1 * | 7/2004 | Schorr | A61B 42/00 | 2/69 |
| 2005/0223471 A1 * | 10/2005 | Griesbach, III | A41D 19/0089 | 2/160 |
| 2006/0093773 A1 * | 5/2006 | Dujardin | B29C 44/5609 | 428/40.1 |
| 2006/0185059 A1 * | 8/2006 | Taha | A41D 19/0089 | 2/170 |
| 2008/0172767 A1 * | 7/2008 | Friedstrom | A47K 7/02 | 2/16 |
| 2009/0246498 A1 * | 10/2009 | Deiss | E04B 1/68 | 428/220 |
| 2010/0017939 A1 * | 1/2010 | Carpenter, Jr. | A41D 19/0034 | 2/160 |
| 2010/0095434 A1 * | 4/2010 | Stuart | A41B 11/008 | 2/247 |
| 2012/0266348 A1 * | 10/2012 | Meginnis | A41B 17/00 | 2/400 |
| 2013/0125900 A1 * | 5/2013 | Taylor | A61M 5/321 | 128/846 |
| 2014/0157475 A1 * | 6/2014 | Smith | A41D 19/0044 | 2/16 |
| 2016/0186016 A1 * | 6/2016 | Taha | C09J 7/21 | 428/41.8 |
| 2016/0376476 A1 * | 12/2016 | Taha | C09J 7/21 | 156/249 |
| 2017/0362471 A1 * | 12/2017 | Cirami | B32B 7/12 | |
| 2019/0086953 A1 * | 3/2019 | Chavannes | G06F 1/1656 | |
| 2020/0359720 A1 * | 11/2020 | Potnis | A41D 19/0048 | |

\* cited by examiner

SYSTEM AND METHOD FOR ENHANCING STERILITY

FIELD OF THE PRESENT DISCLOSURE

This present disclosure relates generally to systems and methods for enhancing sterility, such as enhancing sterility in a surgical environment that exists between a surgical gown and a surgical glove.

BACKGROUND

During certain surgical procedures, maintaining a high degree of sterility in a surgical environment is important for reducing risk of surgical site infection. Reducing the risk of surgical site infection in turn can maximize the overall success of the surgery. A breach of the sterility of a surgical environment can be dangerous for the patient in terms of contamination leading to surgical site infection. Such a potential breach may also lead to a cross contamination of the surgeon and other surgical staff performing the surgical procedures.

One reported source of potential sterile site contamination is where one or more of a surgeon's surgical glove overlaps a sleeved end or a sleeve cuff of the surgical gown. This is thought to occur as a result of two relatively common mechanisms. A first mechanism through which contamination can occur is related to the use of positive pressure suits (e.g., sterile hoods and body-exhaust systems (BESs)) that are typically worn during certain surgical procedures. As just one example, such BESs are typically worn by a surgeon during hip and knee replacement surgery. The permanent implantation of devices into a patient's body requires a high degree of sterility throughout the surgical procedure. Certain studies have shown that the use of such a positive pressure suit helps to decrease the risk of contamination from the surgeon or surgical assistants.

Such sealed positive pressure operating suits are designed to introduce air into a surgeon's hood and operating garment system via a fan and a positive pressure generated above a surgeon's head. Typically, in such a positive pressure environment, exhaust airflow will exit out through the bottom of the surgical gown or surgical garment below a level of the sterile field. Difficulties may arise in such positive pressure operating environments.

As just one example, folds or creases in one or more of the arm sleeves of the surgical garment where the arm sleeve is overlapped by a surgical glove can prevent a fluid or air seal between the surgical glove and the arm sleeve of the surgical garment. Such undesired or unwanted folds and/or creases can allow air to escape or flow out of the pressurized gown system and therefore over an end of the sleeve. One potential disadvantage of such a pressurized gown system leak is that such a leak may result in an accumulation of bacteria on the garment sleeve surface and/or surgical glove.

A second mechanism of potential surgical environment contamination involves an inadvertent separation of the surgical glove from the garment sleeve cuff during the surgical procedure. Separation of the surgical glove relative to the surgical gown results in a separation of the two, exposing a potentially contaminated terminal end of the gown cuff. Separation of the surgical glove relative to the surgical gown may also expose the skin of a surgeon. Such a separation may occur when the surgeon extends his or her arm, thereby placing tension on the surgical glove and the garment sleeve overlap interface. In the course of performing surgery, a surgeon may use different methods of movement, oftentimes extending their reach or moving in a vigorous manor depending on the type of operation. During this type of movement, there is a potential risk that the surgical glove could pull back from and therefore separate from the surgical gown. This could expose a potentially contaminated terminal end of the garment cuff, and hence the skin of the surgeon. There is also a potential contamination risk that the surgical garment or the surgical glove of the surgeon can snag on operating environment surfaces or operating instruments surrounding the surgeon. Such snagging can pull the surgical gown out from the overlapping glove.

As such, there is a general need for systems and methods of enhanced sterility that help to ensure that, during operative procedures, a surgical glove stays in proper position, overlapping the surgical garment as well as creating a fluid or an air seal between a surgical glove and a surgical garment. There is also a general need for a system that will maintains a sealed interface between the surgical gown sleeve end and the surgical glove, resisting positive pressure airflow as well as distractive forces.

SUMMARY

In one system, a system for enhancing sterility comprises a first surgical glove, the first surgical glove comprising an upper glove portion and a lower glove portion, the lower glove portion defining an opening. The system also includes a surgical garment comprising at least one surgical garment cuff and a sealing device comprising a first adhesive. The first adhesive of the sealing device is configured to be affixed between an inside surface of the lower portion of the first surgical glove and an outside surface of the at least one surgical garment cuff so as to provide a fluid seal between the first surgical glove and the at least one surgical garment cuff of the surgical garment.

In one system, the sealing device comprises a circular strip. In one system, the circular strip comprises a first portion and a second portion, wherein the first portion comprises the first adhesive and wherein a first release liner resides over a surface of the first adhesive. The circular strip may comprise a second portion comprising a second adhesive, wherein a second release liner resides over a surface of the second adhesive of the second portion of the circular strip.

In one system, the circular strip is integral to the at least one surgical garment cuff of the surgical garment.

In one system the circular strip is provided along a circumferential interior of the lower glove portion of the first surgical glove.

In one system, the surgical garment comprises at least one reinforced portion. For example, the at least one reinforced portion of the surgical garment comprises a fluid impervious material.

In one system, the first adhesive of the sealing device comprises a pressure sensitive adhesive.

In one system, the system comprises a second surgical glove, wherein the second surgical glove is provided along an outside surface of the at least one surgical garment cuff, and an outer surface of the first surgical glove.

In one system, the surgical garment is part of a positive pressure system.

In one method, a method of increasing sterility comprises the steps of donning a surgical garment comprising at least one surgical garment cuff; removing a first release liner from a first surface of a sealing device and exposing a first adhesive of the sealing device. The method further comprises the step of overlapping at least one portion of the at least one surgical garment cuff of the surgical garment with at least a portion of a first surgical glove and utilizing the first adhesive of the sealing device to provide a fluid seal between the first surgical glove and the at least one surgical garment cuff of the surgical garment.

In one method, the method further comprises the step of eliminating at least one fold in the surgical garment when overlapping the at least one portion of the surgical garment with the portion of the first surgical glove.

In one method, the method further comprises the step of providing the at least one surgical garment cuff of the surgical garment with the sealing device before the sealing device is utilized to provide the fluid seal between the first surgical glove and the at least one surgical cuff of the surgical garment.

In one method, the method further comprises the step of removing a second release liner from a second surface of the sealing device.

In one method, the method further comprises the step of providing an inside of a lower portion of the first surgical glove with the sealing device before the sealing device is utilized to provide the fluid seal between the first surgical glove and the at least one surgical garment cuff.

In one method, the method further comprises the step of configuring the surgical garment as part of a positive pressure system.

In one method, the method further comprises the step of providing a second surgical glove along an outside surface of the at least one surgical garment cuff and an outer surface of the first surgical glove.

The foregoing summary is illustrative only and is not intended to be in any way limiting. In addition to the illustrative aspects, embodiments, and features described above, further aspects, embodiments, and features will become apparent by reference to the figures and the following detailed description.

BRIEF DESCRIPTION OF THE DRAWINGS

Exemplary arrangements are described herein with reference to the drawings, in which:

FIG. 6 is a block diagram of a sealing device, a glove, and a garment cuff, according to an example implementation.

DETAILED DESCRIPTION

Figure 2:
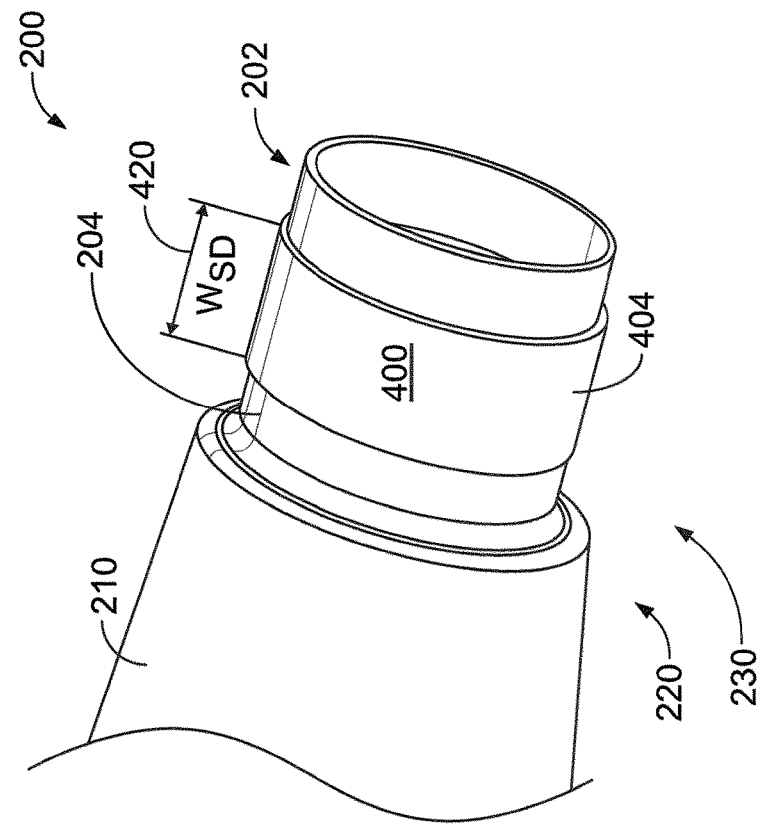
FIG. 2 shows an embodiment of an exemplary surgical garment.

In the following detailed description, reference is made to the accompanying drawings, which form a part hereof. In the drawings, similar symbols typically identify similar components, unless context dictates otherwise. The illustrative arrangements described in the detailed description, drawings, and claims are not meant to be limiting. Other arrangements may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Generally, the present disclosure relates to systems and methods for enhancing the sterility of an operating environment. By utilizing the presently disclosed systems and methods, a heightened sterile operating environment will be achieved. In addition, by utilizing the presently disclosed devices and methods, it will also be ensured that a surgical glove will remain affixed or attached to a sleeve of the surgical garment, while at the same time maintain an air or fluid seal between the surgical glove and the surgical garment. An exemplary surgical glove and surgical garment attachment system employs a circumferential adhesive barrier that functions to seal an inner surface of a lower glove portion to the end of the surgical gown sleeve. This will help to ensure that there is a proper seal between the end of the gown sleeve and the surgical glove, and that the glove remains overlapping the sleeve of the surgical gown under tension due to the strength of the adhesion.

Figure 1:
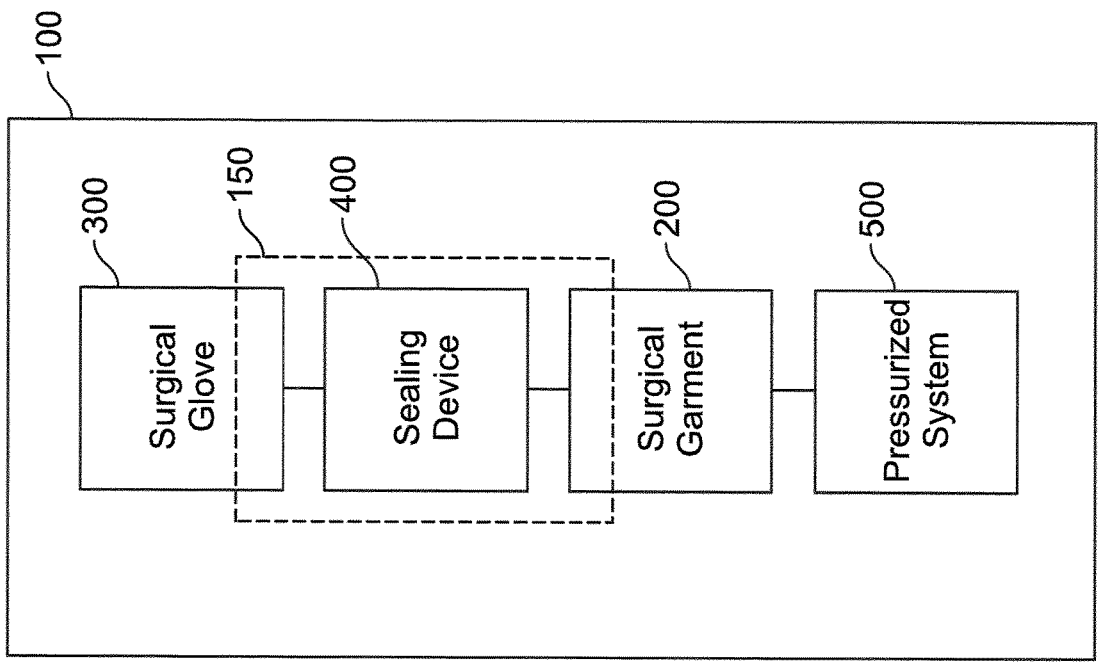
FIG. 1 is a block diagram of a system for enhancing sterility, according to an example implementation.

For example, FIG. 1 is a block diagram of a system 100 for enhancing sterility, according to an example implementation. As just one example, the system 100 may be used to enhance the sterility of an operating environment. As illustrated, the system 100 comprises a first surgical glove 300. The first surgical glove 300 comprises an upper glove portion 302 and a lower glove portion 304. The upper glove portion 302 defines an opening 306. (see, e.g. FIG. 3) The system 100 further includes a surgical garment 200 comprising at least one surgical garment cuff 202. (see, e.g. FIG. 2) The system 100 further comprises a sealing device 400 comprising a first adhesive 402. (see, e.g. FIG. 4) The sealing device 400 is positioned between a portion of the first surgical glove 200 and the surgical garment 300. The sealing device 400 may be integral to the surgical garment 200, the surgical glove 300, integral to both the surgical garment 200 and the surgical glove 300, or it may be a separate, standalone device.

As will be described in greater detail herein, in one preferred arrangement, the first adhesive 408 of the sealing device 400 is configured to be affixed between an inside surface of the lower glove portion of the first surgical glove 300 and an outside surface of the at least one surgical garment cuff 202 so as to provide a fluid seal 150 between the first surgical glove 300 and the at least one surgical garment cuff 202 of the surgical garment 200.

For example, FIG. 2 shows an embodiment of an exemplary surgical garment 200 that may be used in a system for enhancing sterility, such as the system 100 illustrated in FIG. 1. The surgical garment 200 includes at least a first surgical cuff 202 wherein this first surgical cuff 202 comprises an outer surface 204. In one embodiment, the sealing device 400 is positioned or placed along a portion of this outer surface 204 along the garment cuff 202 of the sleeve of the surgical garment 200. In one preferred arrangement, the sealing device 400 will be integrated into the garment during a production process of the surgical garment itself. For example, the sealing device 400 could be stitched into or otherwise fabricated into the material making up the surgical cuff 202. In this illustrated arrangement, the sealing device 400 takes the form of a circular strip 404. Circular in that the sealing device 400 wraps around an entire circumference of the outer surface 204 of the surgical cuff 202. The surgical garment may also comprise at least one reinforced portion 220, such as a fluid impervious material 230.

Figure 4:
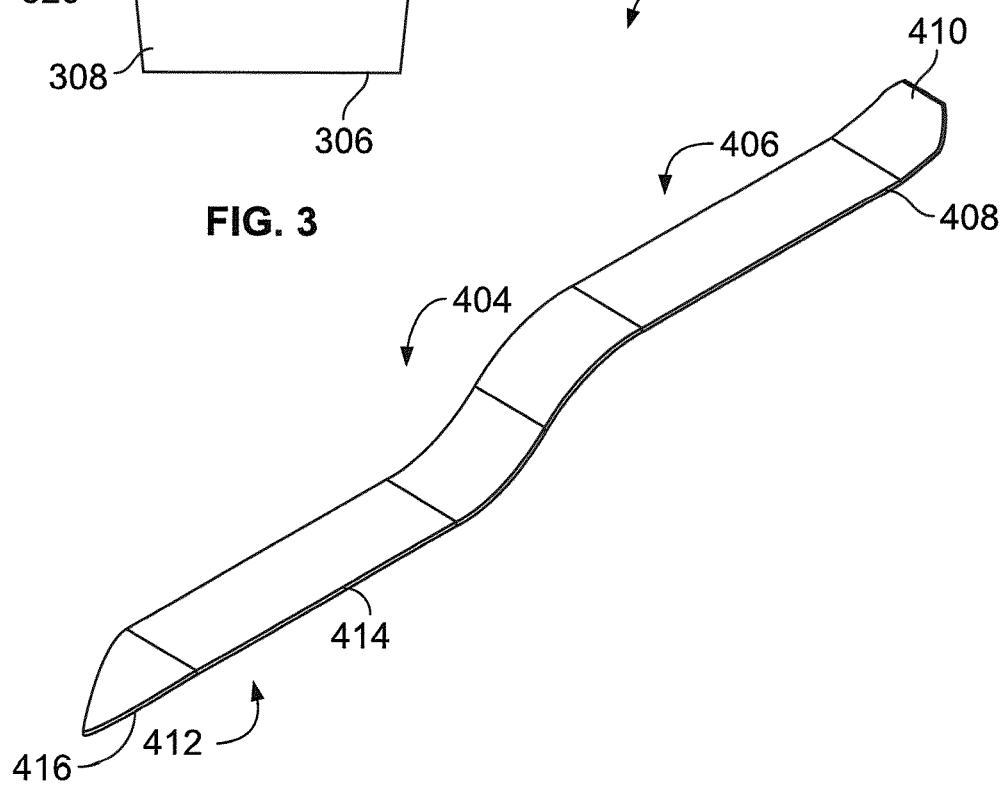
FIG. 4 shows an embodiment of an exemplary sealing device.

For example, FIG. 4 illustrates an embodiment of an exemplary a sealing device 400 such as the sealing device illustrated in FIG. 2. As illustrated, the sealing device 400 comprises a first or a top portion 406 and also comprises a second or a bottom portion 412. The first or top portion comprises a first adhesive 408. In one preferred arrangement, along a top surface of the first adhesive 408 a first release liner 410 (e.g., a tear away paper covering) is provided. The first release liner 410 acts to protect the first adhesive 408 and can be manually removed or torn away so as to expose the first adhesive 408. The release liner 410 could be a waxy paper that would protect the first adhesive 408 until a surgeon is ready to expose the first adhesive 408 to either the surgical glove or the surgical garment.

In one arrangement, the sealing device 400 comprises both a first and a second adhesive. For example, in sealing device 400 illustrated in FIG. 4, the second or a bottom portion 412 comprises a second adhesive 414. Along a bottom surface of the second adhesive 414 a second release liner 416 (similar to the first release liner) is provided. The second release liner 416 acts to protect the second adhesive 414 and can be manually removed or torn away so as to uncover the second adhesive 414. The second adhesive 414 may be the same or may be different than the first adhesive 408.

The thickness of this sealing device 400 could range from 0.001 inches to as much as 2 inches. The width $W_{SD}$ 420 of the sealing device 400 could range from 0.25 inches to 4 inches. Once either the first or the second adhesive 408, 414 of the sealing device 400 is exposed, the surgeon will put on the surgical glove 300 by overlapping the lower portion of the surgical glove over the cuff of the surgical garment so as that the now exposed adhesive can fixedly secure the surgical glove 300 to the surgical garment 200. In addition, the adhesive of the sealing device 400 that secures the surgical garment 200 to the surgical glove 300 also provides a fluid seal 150 between the surgical glove 300 and the cuff of the surgical garment 200.

Figure 3:
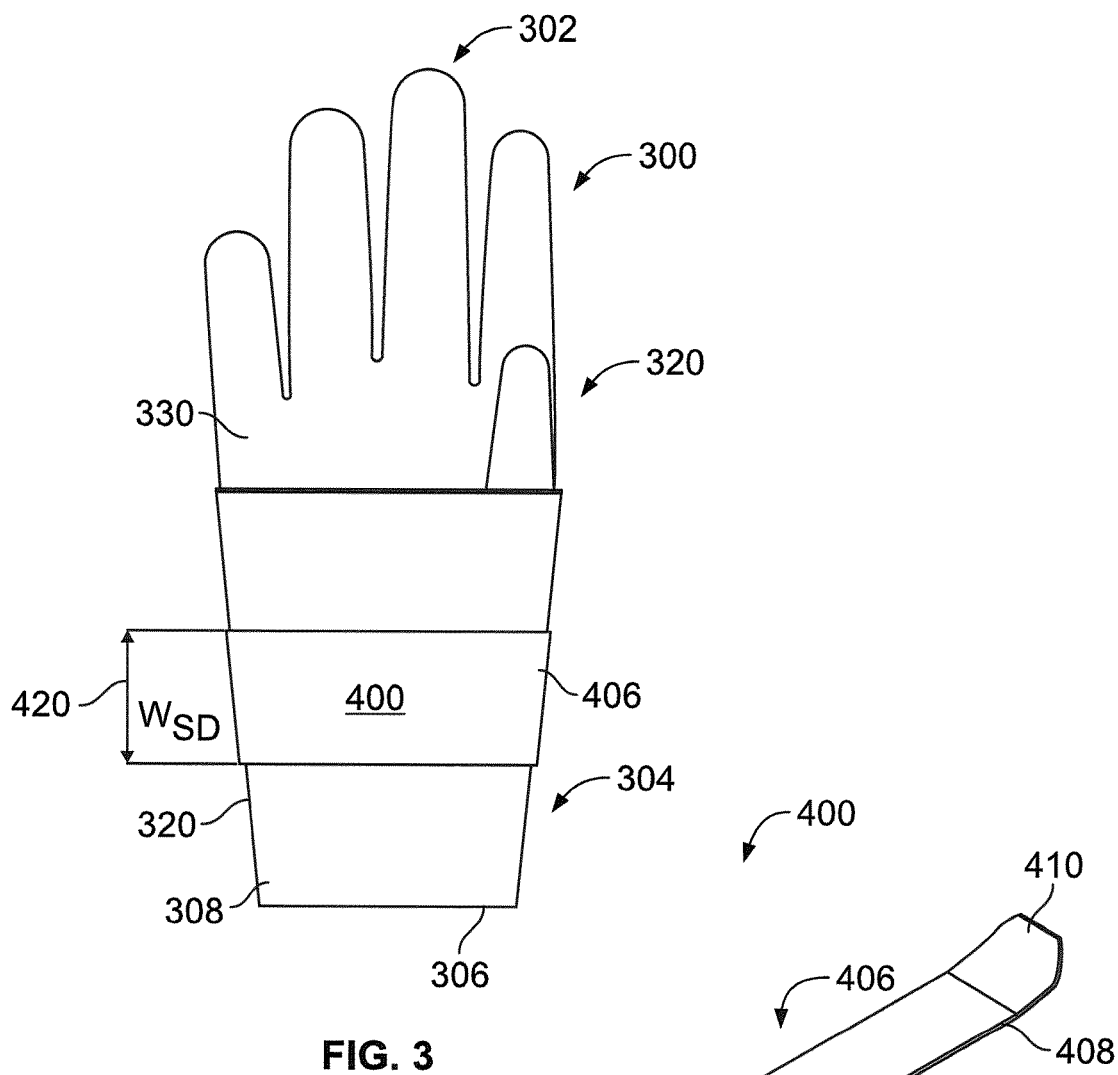
FIG. 3 shows an embodiment of an exemplary surgical glove.

FIG. 3 illustrates an embodiment of an exemplary surgical glove 300. As illustrated, the surgical glove 300 comprises an upper glove portion 302 and a lower glove portion 304. Near the lower glove portion 304, the surgical glove 300 defines an opening 306. The surgical glove 300 illustrated with a sealing device 400 that may be integrated into the surgical glove 300. For example, in FIG. 3, sealing device 400 is provided along an inner surface 308 of the surgical glove 300. In this illustrated arrangement, the bottom or lower portion 304 of the surgical glove 300 is illustrated as being folded over, back onto the surgical glove 300. In such a folded over position, an inner surface 308 of the surgical glove 300 is shown. Provided along this inner surface 308 of the surgical glove 300 is a sealing device 400.

In another arrangement, the sealing device 400 is integrated into an inside cuff of a surgical glove instead of the outside cuff of the surgical garment. In such an arrangement, the sealing device 400 may also comprise a circular strip of adhesive with a thickness ranging from 0.001 inches to 2 inches. The width of the sealing device 400 could range from 0.25 inches to 4 inches. The cuff of the surgical glove could be lengthened to accommodate this sealing device on the glove as well. This sealing device could be integrated into a surgical glove during the manufacturing process and can be protected by a waxy paper or another type of cover to protect it until the adhesive needs to be applied. Once the surgeon is ready to adhere the glove to the surgical garment, the protective covering or release liner is removed and the surgical glove can then be pulled over the cuff of the garment and then releasably secured to the cuff. The elastic nature of the surgical glove will ensure that a fluid seal will be established.

In yet another embodiment, the sealing device 400 will comprise a standalone product similar to single sided or double sided adhesive tape. In such an embodiment, the adhesive will be placed on one or both sides of a strip of material that could be but is not limited to Teflon or an antimicrobial material. It could also be, but is not limited to, an adhesive foam tape comprised of urethane or polyurethane.

The single or double sided adhesive strip could have a length as long as two feet and a thickness ranging from 0.001 inches to 2 inches. The width of the adhesive strip could range from 0.25 inches to 4 inches. Both sides of the strip can be covered by waxy paper or another type of cover for protection. Once a surgeon is ready to apply the adhesive, one side will be exposed and applied to either the outside cuff of the gown or the inside cuff of the glove according to the surgeon's preference. The adhesive strip will be applied to the region where the surgical glove overlaps the surgical garment. Then the other side of the adhesive will be exposed and applied to the other surface that needs to complete the seal.

Different adhesive types may be used for different situations and according to the preference of the surgeon. For example, the first adhesive provided on the first portion of the sealing device 400 may be the same or may be different than the second adhesive provided on the second portion of the sealing device 400.

The adhesives could be but are not limited to, a pressure sensitive adhesive (PSA), a fabric type adhesive like polyvinyl acetate (PVA), or a tackier globular type adhesive. A more globular adhesive could be used to fill in the creases left by a surgeon using a gown that has cuffs that are too big for his/her wrists. This more globular type adhesive could be but is not limited to, a foam type of adhesive that expands after it is administered to seal any cracks.

The presently disclosed systems and methods create a fluid seal between the sleeve of the surgeon's gown and the surgical glove. In certain situations, surgeons wear an apparatus that pumps air through their gown, creating a positive air flow that vents out the bottom of the gown. These are known as positive pressure suits. In these positive pressure suits, air is known to escape out from the creases or folds that may exist where the surgical gloves and the sleeves of the surgical garment overlap. While in surgery, bacteria can accumulate in these crevices due to the positive air flow escaping through the creases between the glove and sleeve of the gown. The presently disclosed system and methods will help prevent the flow of air in or out of the surgeon's gown in the crease where the gloves overlap with the sleeve, thereby ceasing the contamination problem due to air escaping out from the crease where the gloves and the sleeve overlap.

Prior to performing a surgical procedure, a surgeon may layer the glove and surgical garment utilizing different methods. For example, in one situation, a surgeon will first put on a first surgical glove. Then, the surgeon will don a surgical garment or surgical garments. Once the garment is on, the surgeon can optionally place a second surgical glove on so that the cuff of the surgical garment will be sandwiched between the first surgical glove and the second surgical glove.

Alternatively, the surgeon may don the surgical garment first. Then, the surgeon will put on the first surgical glove. Then, optionally, the surgeon will put on a second surgical glove. In such a situation, there would be two layers of gloves (the first surgical glove and the second surgical glove) that are placed over the cuff of the surgical garment.

Figure 5:
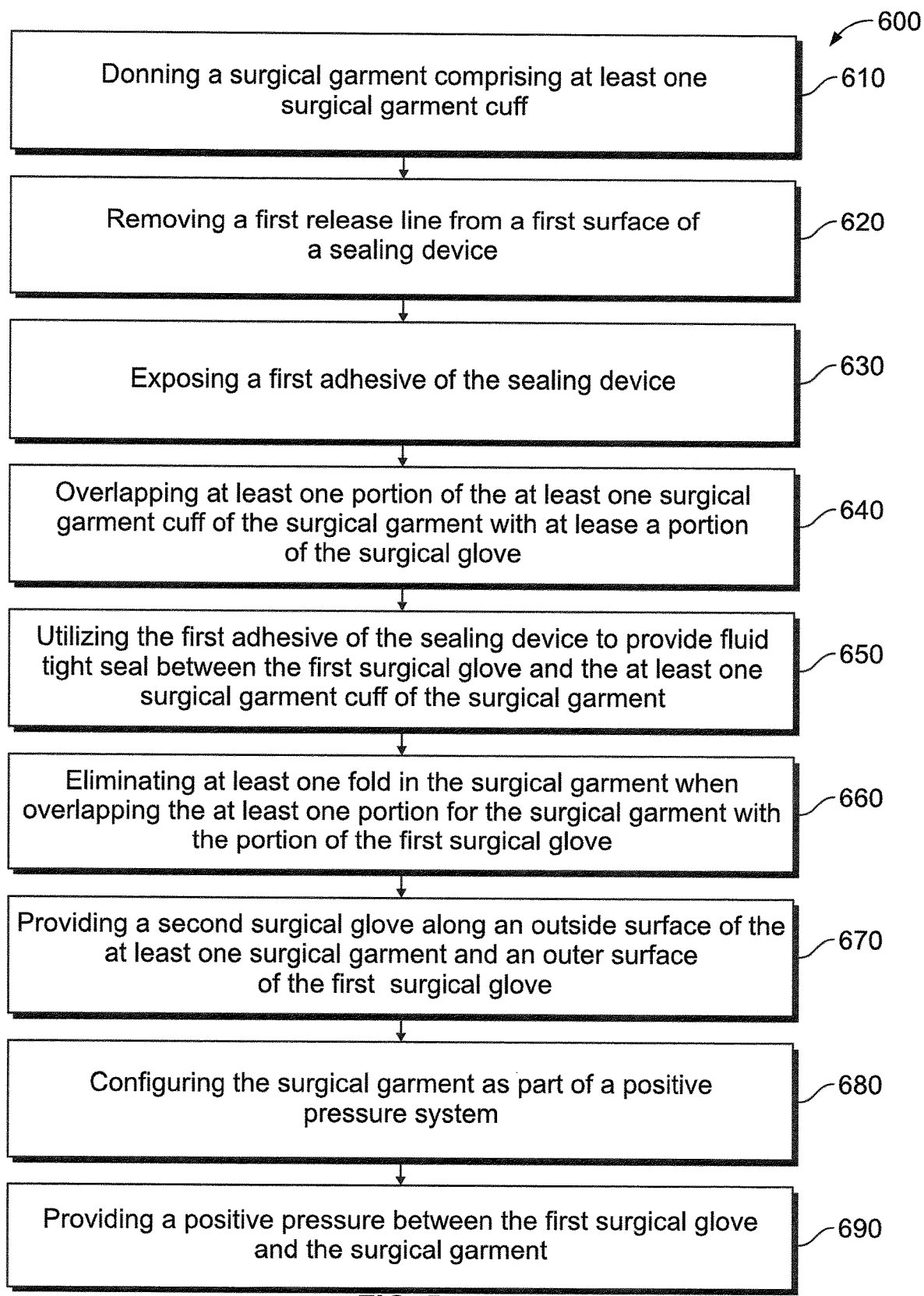
FIG. 5 shows a flowchart of an example method, according to an example implementation.

FIG. 5 shows a flowchart of an example method 600, according to an example implementation. Specifically, FIG. 5 illustrates a method 600 of enhancing sterility, for example, enhancing sterility in an operating environment. Method 600 may include one or more operations, functions, or actions as illustrated by one or more of blocks in FIG. 5. Although the blocks are illustrated in a sequential order, these blocks may also be performed in parallel, and/or in a different order than those described herein. Also, the various blocks may be combined into fewer blocks, divided into additional blocks, and/or removed based upon the desired implementation. It should be understood that for this and other processes and methods disclosed herein, flowcharts show functionality and operation of one possible implementation of present examples.

At block 610, the method 600 includes donning a surgical garment 200 comprising at least one surgical garment cuff 202. In one preferred method, the method 600 further comprises the step of providing the at least one surgical garment cuff 202 of the surgical garment 200 with a sealing device 400 before the sealing device 400 is utilized to provide a fluid seal 150 between a first surgical glove 300 and the at least one surgical cuff 202 of the surgical garment 200.

In yet another preferred arrangement, the method 600 comprises the step of providing an inside of a lower portion 304 of a first surgical glove 300 with a sealing device 400 before the sealing device 400 is utilized to provide a fluid seal 150 between the first surgical glove 300 and the at least one surgical garment cuff 200.

After block 610, the method 600 includes the step of removing a first release liner 410 from a first surface of a sealing device at block 620. As noted herein, the sealing device 400 may be provided either on the cuff 202 of the surgical garment 200 or on the surgical glove 300.

After block 620, the method 600 includes the step of exposing a first adhesive of the sealing device at step 630. After block 630, the method 600 includes the step of overlapping at least one portion of the at least one surgical garment cuff 202 of the surgical garment 200 with at least a portion of a first surgical glove 300 at block 640.

After block 640, the method 600 includes the step of utilizing the first adhesive of the sealing device 400 to provide a fluid seal 150 between the first surgical glove 300 and the at least one surgical garment cuff 202 of the surgical garment at block 650. After block 650, the method 600 includes the step of eliminating at least one fold in the surgical garment 200 when overlapping the at least one portion of the surgical garment 200 with the portion 304 of the first surgical glove at step 660.

After block 660, there is an optional step at block 670. At block 670, the method 600 includes the optional step of providing a second surgical glove 300 along an outside surface 204 of the at least one surgical garment cuff 202 and an outer surface 330 of the first surgical glove 300. The second surgical glove 300 may or may not be the same type of surgical glove as the first surgical glove 300.

After optional block 670, the method 600 includes the step of configuring the surgical garment 200 as part of a positive pressure system 500 at block 680. After block 680, the method 600 includes the step of providing a positive pressure between the first surgical glove 300 and the surgical garment 200 at step 690.

Figure 6:
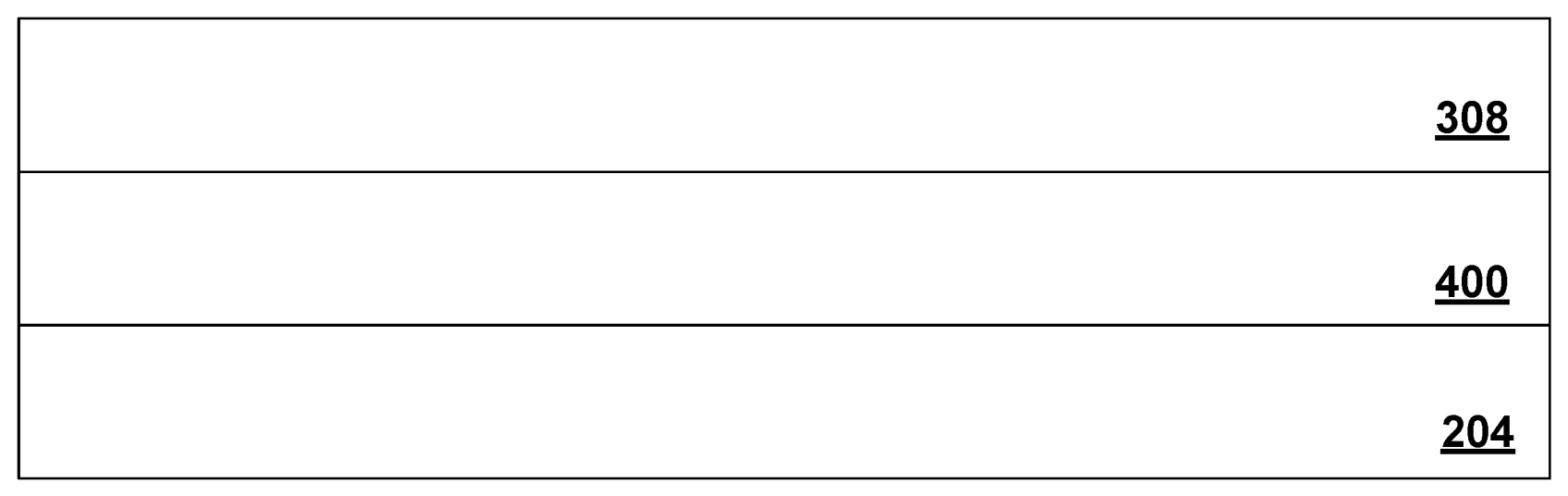

FIG. 6 shows the sealing device 400 between the inner surface 308 of the surgical glove and an outside surface 204 of the surgical garment cuff.

It should be understood that the illustrated components are intended as an example only. In other example embodiments, fewer components, additional components, and/or alternative components are possible as well. Further, it should be understood that the above described and shown embodiments of the present disclosure are to be regarded as non-limiting examples and that they can be modified within the scope of the claims.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims, along with the full scope of equivalents to which such claims are entitled. It is also to be understood that the terminology used herein is for the purpose of describing particular embodiments only, and is not intended to be limiting.

We claim:

1. A system comprising:
   a surgical glove,
   a surgical garment comprising a sleeve and a surgical garment cuff that is distal to the sleeve at a distal end of the surgical garment, wherein the sleeve has a first diameter and the surgical garment cuff has a second diameter that is less than the first diameter, and
   a sealing device comprising an adhesive on a first side of the sealing device or on a second side of the sealing device that is opposite the first side,
      the first side being configured to be applied on an inside surface of the surgical glove, and
      the second side being configured to be applied on an outside surface of the surgical garment cuff such that the second diameter is present on a distal side of the sealing device and present on a proximal side of the sealing device and such that the sealing device provides a fluid seal between the inside surface and the outside surface with the fluid seal being formed on an entire circumference of the outside surface, wherein the sealing device is a single strip of material,
   wherein the surgical garment cuff comprises a reinforced portion comprising a fluid impervious material, wherein the sealing device is configured to provide the fluid seal between the fluid impervious material of the reinforced portion and the inside surface of the surgical glove.

2. The system of claim 1, wherein the adhesive provides the fluid seal on the entire circumference of the outside surface.

3. The system of claim 2, wherein the sealing device takes a form of a strip that is provided along the inside surface.

4. The system of claim 1, wherein the adhesive comprises a globular adhesive.

5. The system of claim 1, the second side being configured to be applied on the outside surface of the surgical garment cuff so as to provide the fluid seal with the fluid seal being formed on an entire circumference of the inside surface.

6. The system of claim 1, wherein the adhesive comprises a foam adhesive.

7. The system of claim 1, wherein the adhesive is configured to expand after the adhesive is administered.

8. The system of claim 1, wherein the fluid seal is an air seal.

9. The system of claim 1, wherein the fluid seal is configured to maintain a positive air pressure within the surgical garment and the surgical glove relative to outside the surgical garment and the surgical glove.

10. The system of claim 1, wherein the sealing device is configured to provide the fluid seal via the sealing device forming a closed loop via a first end of the sealing device contacting a second end of the sealing device that is opposite the first end.

\* \* \* \* \*